(12) United States Patent
Ankersen et al.

(10) Patent No.: US 6,566,337 B1
(45) Date of Patent: May 20, 2003

(54) COMPOUNDS WITH GROWTH HORMONE RELEASING PROPERTIES

(75) Inventors: Michael Ankersen, Frederiksberg (DK); Lutz Stefan Richter, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/431,864

(22) Filed: Nov. 2, 1999

Related U.S. Application Data
(60) Provisional application No. 60/107,663, filed on Nov. 9, 1998.

(30) Foreign Application Priority Data

Nov. 3, 1998 (DK) .......................................... 1998 01414

(51) Int. Cl.⁷ ............................................. A61K 38/05
(52) U.S. Cl. .......................... 514/19; 562/445; 562/553
(58) Field of Search .......................... 514/19; 562/445, 562/553

(56) References Cited

U.S. PATENT DOCUMENTS
5,977,178 A    11/1999    Hansen et al. .............. 514/616

FOREIGN PATENT DOCUMENTS
WO    WO 97/23508    7/1997

*Primary Examiner*—Christopher S. F. Low
*Assistant Examiner*—David Lukton
(74) *Attorney, Agent, or Firm*—Cheryl H. Agris; Reza Green

(57) ABSTRACT

This invention relates to novel compounds, compositions containing them, and their use for treating medical disorders resulting from a deficiency in growth hormone.

14 Claims, No Drawings

COMPOUNDS WITH GROWTH HORMONE RELEASING PROPERTIES

CROSS-REFERENCE TO RELATED APPLICATIONS

This application is a continuation of application Ser. No. 60/107,663 filed on Nov. 9, 1998 and claims priority under 35 U.S.C. 119 of Danish application no. 1998 01414 filed on Nov. 3, 1998, the contents of which are fully incorporated herein by reference.

FIELD OF INVENTION

The present invention relates to novel compounds, compositions containing them, and their use for treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilisation and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyctase activating peptide), muscarinic receptor agonists and a synthetic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration non-viable. Furthermore, other directly acting natural secretagogues, e.g., GHRH and PACAP, are longer polypeptides for which reason parenteral administration is preferred.

The use of certain compounds for increasing the levels of growth hormone in mammals has previously been proposed, e.g. in EP 18 072, EP 83 864, WO 8302272, WO 8907110, WO 8901711, WO 8910933, WO 8809780, WO 9118016, WO 9201711, WO 9304081, WO 9413696, WO 9517423, WO 9514666, WO 9615148, WO 9622997, WO 9635713, WO 9700894, WO 9722620, WO 9723508, WO 9740023, and WO 9810653.

The composition of growth hormone releasing compounds is important for their growth hormone releasing potency as well as their bioavailability. It is therefore an object of the present invention to provide novel compounds with growth hormone releasing properties. Moreover, it is an object to provide novel growth hormone releasing compounds (growth hormone secretagogues) which are specific and/or selective and have no or substantially no side-effects, such as e.g. release of LH, FSH, TSH, ACTH, vasopressin, oxytocin, cortisol and/or prolactin. It is also an object to provide compounds which have good oral bioavailability. A further object of the present invention is to provide compounds with a relatively short plasma elimination half-life. A still further object of the present invention is to provide compounds which have a good oral biovailability together with a relatively short plasma elimination half-life.

SUMMARY OF THE INVENTION

In accordance with the present invention there is provided novel compounds which act directly on the pituitary cells under normal experimental conditions in vitro to release growth hormone therefrom.

These growth hormone releasing compounds can be utilized in vitro as unique research tools for understanding, inter alia, how growth hormone secretion is regulated at the pituitary level.

Moreover, the growth hormone releasing compounds of the present invention can also be administered in vivo to increase endogenous growth hormone release.

DESCRIPTION OF THE INVENTION

Accordingly, the present invention relates to a compound of the general formula I formula I

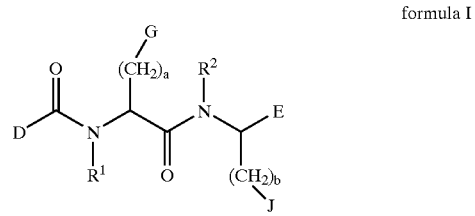

wherein $R^1$ and $R^2$ are independently hydrogen or $C_{1-6}$-alkyl optionally substituted with aryl;

a and b are independently 1 or 2;

G is

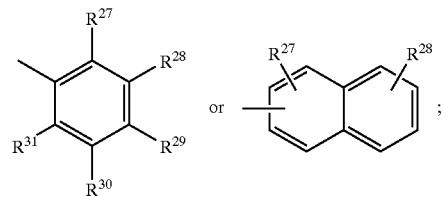

J is

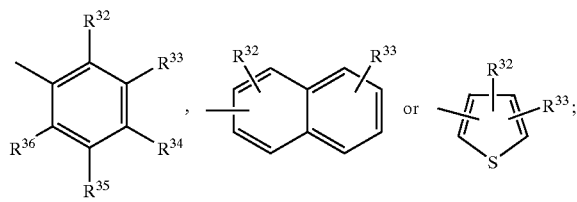

wherein $R^{27}$, $R^{28}$, $R^{29}$, $R^{30}$, $R^{31}$, $R^{32}$, $R^{33}$, $R^{34}$, $R^{35}$ and $R^{36}$ independently are hydrogen, halogen, aryl, $C_{1-6}$-alkyl or $C_{1-6}$-alkoxy;

D is

R$^7$—NH—(CR$^8$R$^9$)$_p$—(CH$_2$)$_m$—M—(CHR$^{10}$)$_q$—(CH$_2$)$_n$— wherein R$^7$, R$^8$, R$^9$ and R$^{10}$ are independently hydrogen or C$_{1-6}$ alkyl optionally substituted with halogen, amino, hydroxyl or aryl;

R$^7$ and R$^8$ or R$^7$ and R$^9$ or R$^8$ and R$^9$ may optionally form —(CH$_2$)$_i$—U—(CH$_2$)$_j$—, wherein i and j are independently are 1 or 2 and U is —O—, —S— or a valence bond;

m and n are independently 0, 1, 2, or 3;

p and q are independently 0 or 1;

M is —CR$^{11}$=CR$^{11a}$—, arylene, —O—, or —S—;

R$^{11}$ and R$^{11a}$ are independently hydrogen, or C$_{1-6}$-alkyl optionally substituted with aryl;

E is

—CONR$^{12}$R$^{13}$, wherein

R$^{12}$ is C$_{1-6}$-alkyl;

R$^{13}$ is hetaryl or C$_{1-6}$-alkyl substituted with hetaryl;

or a pharmaceutically acceptable salt thereof.

Moreover, the compounds of formula I may comprise any optical isomers thereof, in the form of separated, pure or partially purified optical isomers or racemic mixtures thereof. Whenever one or more chiral carbon atoms are present such chiral center or centers may be in the R- and/or S-configuration, or a mixture of R and S.

Furthermore, the compounds of formula I may have one or more carbon-carbon double bonds with the possibility of geometric isomeri, and it is intended that possible stereoisomers (E or Z isomers) are included in the scope of the invention, unless a special geometric isomer is specified.

In one embodiment of the compound of formula I R$^1$ is C$_{1-6}$-alkyl, such as C$_{1-4}$-alkyl, in particular methyl.

In a further embodiment of the compound of formula I R$^2$ is C$_{1-6}$-alkyl, such as C$_{1-4}$-alkyl, in particular methyl.

In a still further embodiment of the compound of formula I a is 1.

In a further embodiment of the compound of formula I b is 1.

In a still further embodiment of the compound of formula I G is

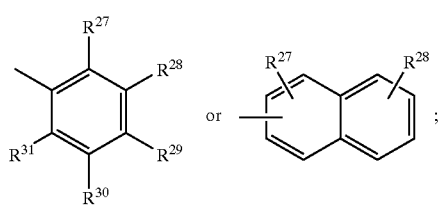

wherein R$^{27}$, R$^{28}$, R$^{29}$, R$^{30}$ and R$^{31}$ independently are hydrogen, halogen, aryl, C$_{1-6}$-alkyl or C$_{1-6}$-alkoxy. In one embodiment R$^{27}$ is hydrogen. In a second embodiment R$^{28}$ is hydrogen. In a third embodiment R$^{29}$ is hydrogen. In a further embodiment R$^{30}$ is hydrogen. In a still further embodiment R$^{31}$ is hydrogen. In the compound of the above formula I G is preferably phenyl or naphthyl, in particular 2-naphthyl.

In a further embodiment of the compound of formula I J is

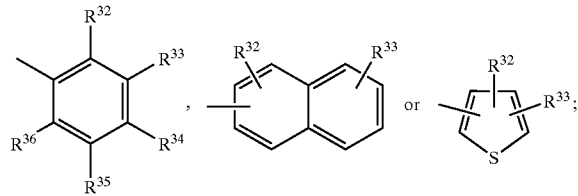

wherein R$^{32}$, R$^{33}$, R$^{34}$, R$^{35}$ and R$^{36}$ independently are hydrogen, halogen, aryl, C$_{1-6}$alkyl or C$_{1-6}$-alkoxy. In one embodiment R$^{32}$ is hydrogen. In a second embodiment R$^{33}$ is hydrogen. In a third embodiment R$^{34}$ is hydrogen. In a further embodiment R$^{35}$ is hydrogen. In a still further embodiment R$^{36}$ is hydrogen. In the compound of the above formula I J is preferably naphthyl, thienyl or phenyl, in particular phenyl.

In a still further embodiment of the compound of formula I D is

R$^7$—NH—(CR$^8$R$^9$)$_p$—(CH$_2$)$_m$—M—(CHR$^{10}$)$_q$—(CH$_2$)$_n$— wherein R$^7$, R$^8$, R$^9$ and R$^{10}$ are independently hydrogen or C$_{1-6}$ alkyl optionally substituted with halogen, amino, hydroxyl or aryl;

m and n are independently 0, 1, 2, or 3;

p and q are independently 0 or 1;

M is —CR$^{11}$=CR$^{11a}$—, aryl, —O—, or —S—;

R$^{11}$ and R$^{11a}$ are independently hydrogen, or C$_{1-6}$-alkyl optionally substituted with aryl. In one embodiment R$^7$ is hydrogen. In a second embodiment R$^7$ is C$_{1-6}$-alkyl, such as C$_{1-4}$-alkyl, in particular methyl. In a third embodiment R$^8$ is hydrogen. In a further embodiment R$^8$ is C$_{1-6}$-alkyl, such as C$_{1-4}$-alkyl, in particular methyl. In a still further embodiment R$^9$ is hydrogen. In a further embodiment R$^9$ is C$_{1-6}$-alkyl, such as C$_{1-4}$-alkyl, in particular methyl. In a still further embodiment R$^{10}$ is hydrogen. In a further embodiment R$^{10}$ is C$_{1-6}$-alkyl, such as C$_{1-4}$-alkyl, in particular methyl. In a further embodiment n is 0. In a still further embodiment q is 0. In a further embodiment m is 1. In a still further embodiment p is 1. In a further embodiment M is —CR$^{11}$=CR$^{11a}$—. In a still further embodiment M is —CH=CH—. In a further embodiment M is —C(CH$_3$)=CH—. In a still further embodiment R$^{11}$ is hydrogen. In a further embodiment R$^{11}$ is C$_{1-6}$-alkyl, such as C$_{1-4}$-alkyl, in particular methyl. In a still further embodiment R$^{11a}$ is hydrogen. In a further embodiment R$^{11a}$ is C$_{1-6}$-alkyl, such as C$_{1-4}$-alkyl, in particular methyl. In the compound of the above formula I D is preferably H$_2$N—C(CH$_3$)$_2$—CH$_2$—CH=CH—, in particular the E isomer of H$_2$N—C(CH$_3$)$_2$—CH$_2$—CH=CH—.

In a further embodiment of the compound of formula I E is —CONR$^{12}$R$^{13}$, wherein R$^{12}$ is C$_{1-6}$-alkyl;

R$^{13}$ is hetaryl or C$_{1-6}$-alkyl substituted with hetaryl. In one embodiment R$^{12}$ is C$_{1-4}$-alkyl, in particular methyl. In a second embodiment R$^{13}$ is C$_{1-6}$-alkyl substituted with pyridinyl, such as C$_{1-4}$-alkyl substituted with pyridinyl, in particular ethyl substituted with pyrdinyl. In a third embodiment R$^{13}$ is ethyl substituted with 2-pyridinyl. In a further embodiment R$^{13}$ is ethyl substituted with 4-pyridinyl. In the compound of the above formula I E is preferably —CON(CH$_3$)R$^{13}$, in which R$^{13}$ is 2-(4-pyridinyl)-ethyl or 2-(2-pyridinyl)-ethyl.

In a still further embodiment of the compound of formula I

D is H₂N—C(CH₃)₂—CH₂—CH=CH—; and

E is —CON(CH₃)R¹³ wherein $R^{13}$ is $C_{1-6}$-alkyl substituted with pyridinyl.

Any possible combination of two or more of the embodiments described herein is comprised within the scope of the present invention.

Preferred compounds of formula I of the invention are:
(2E)-5-Amino-5-methylhex-2-enoic acid N-methyl-N-[(1R)-1-(N-methyl-N-{(1R)-1-[N-methyl-N-(2-(2-pyridinyl)ethyl)carbamoyl]-2phenylethyl}carbamoyl)-2-(2-naphthyl) ethyl]amide

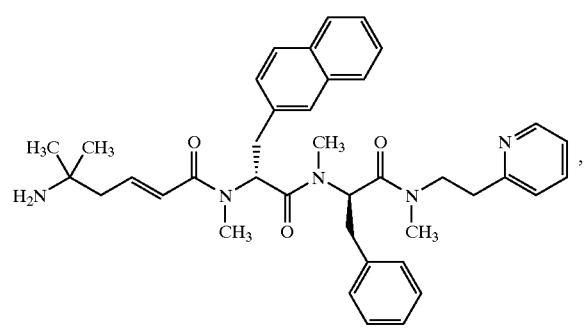

(2E)-5-Amino-5-methylhex-2-enoic acid N-methyl-N-[(1R)-1-(N-methyl-N-{(1R)1-[N-methyl-(2-(4-pyridinyl)ethyl)carbamoyl]-2-phenylethyl}carbamoyl)-2-(2-naphthyl)ethyl]amide

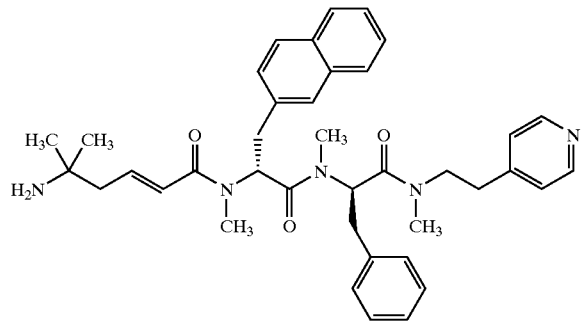

and pharmaceutically acceptable salts thereof.

General Method

The method illustrated in below scheme I is by no mean intended to limit the present invention in any aspect, but should only be seen as a guidance for how the present compounds may be prepared.

Scheme I

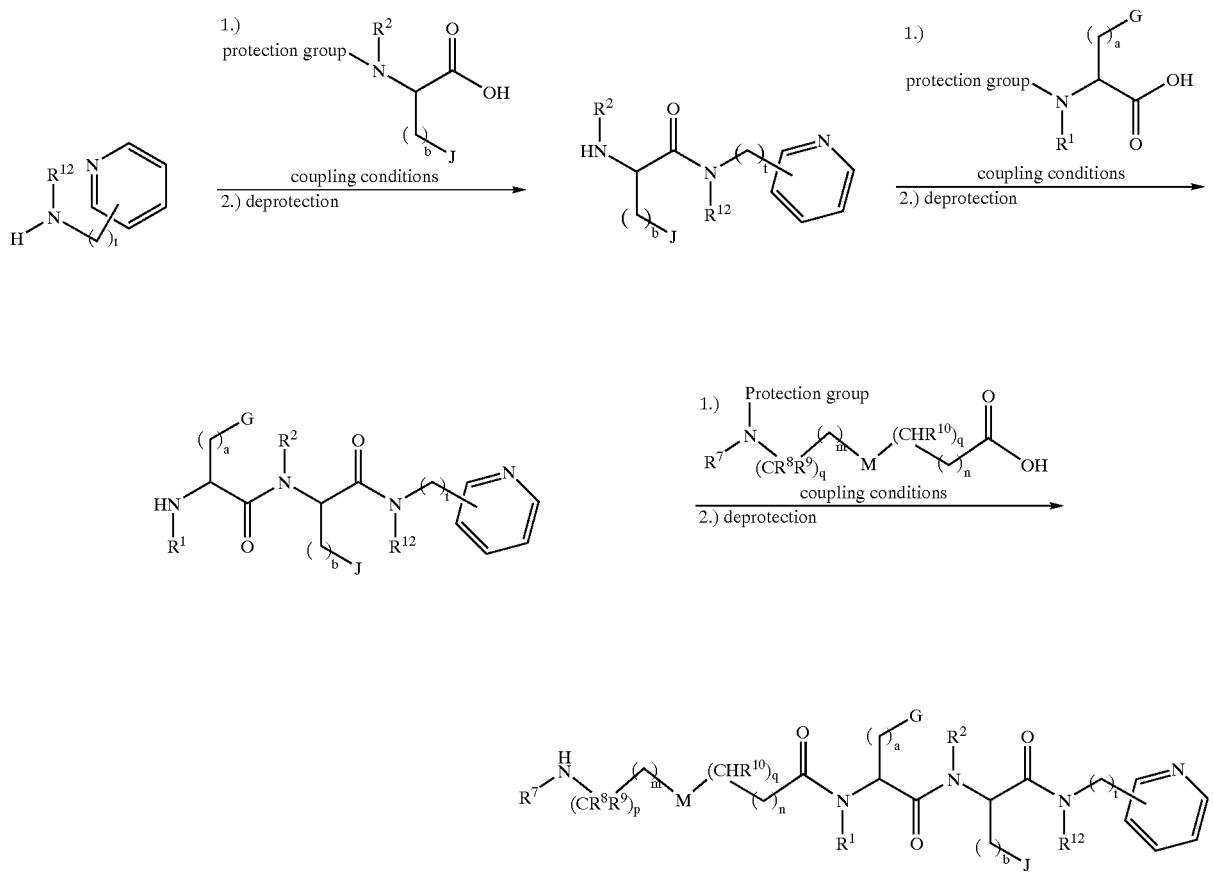

Compounds of the type of formula I may be synthesized by coupling of an amine of type

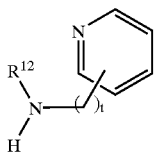

(wherein t is 0, 1, 2, 3, 4, 5, or 6) and a suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane (cf. scheme I). The product may be deprotected at the nitrogen of the acid by a method known for a person skilled in the art and described in the literature e.g. in T. W. Greene, P. G. M. Wuts Protective groups in organic synthesis, $2^{nd}$ edition, Wiley, N.Y. The product is coupled with a suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane. The product may be deprotected at the nitrogen of the acid by a method known for a person skilled in the art and described in the literature e.g. in T. W. Greene, P. G. M. Wuts Protective groups in organic synthesis, $2^{nd}$ edition, Wiley, N.Y. The product is coupled with a suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane. All protection groups may be removed by a method known for a person skilled in the art and described in the literature e.g. in T. W. Greene, P. G. M. Wuts Protective groups in organic synthesis, $2^{nd}$ edition, Wiley, N.Y.

The compounds of formula I exhibit an improved resistance to proteolytic degradation by enzymes because they are non-natural, in particular because the natural amide bonds are replaced by non-natural amide bond mimetics. The increased resistance to proteolytic degradation of the compounds of the invention in comparison with known hormone releasing peptides is expected to improve their bioavailability compared to that of the peptides suggested in the prior literature.

In the above structural formulas and throughout the present specification, the following terms have the indicated meanings:

The $C_{1-6}$-alkyl, $C_{1-6}$-alkylene, $C_{1-4}$-alkyl or $C_{1-4}$-alkylene groups specified above are intended to include those alkyl or alkylene groups of the designated length in either a linear or branched or cyclic configuration. Examples of linear alkyl are methyl, ethyl, propyl, butyl, pentyl, and hexyl and their corresponding divalent moieties, such as ethylene. Examples of branched alkyl are isopropyl, sec-butyl, tert-butyl, isopentyl, and isohexyl and their corresponding divalent moieties, such as isopropylene. Examples of cyclic alkyl are $C_{3-6}$-cycloalkyl such as cyclopropyl, cyclobutyl, cyclopentyl and cyclohexyl and their corresponding divalent moieties, such as cyclopropylene.

The $C_{1-6}$-alkoxy groups specified above are intended to include those alkoxy groups of the designated length in either a linear or branched or cyclic configuration. Examples of linear alkoxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are $C_{3-6}$-cycloalkoxy such as cyclopropyloxy, cyclobutyloxy, cyclopentyloxy and cyclohexyloxy.

In the present context, the term "aryl" is intended to include monovalent carbocyclic aromatic ring moieties, being either monocyclic, bicyclic or polycyclic, e.g. selected from the group consisting of phenyl and naphthyl, optionally substituted with one or more $C_{1-6}$-alkyl, $C_{1-6}$-alkoxy, halogen, amino or aryl.

In the present context, the term "arylene" is intended to include divalent carbocyclic aromatic ring moieties, being either monocyclic, bicyclic or polycyclic, e.g. selected from the group consisting of phenylene and naphthylene, optionally substituted with one or more $C_{1-6}$-alkyl, $C_{1-6}$-alkoxy, halogen, amino or aryl.

In the present context, the term "hetaryl" is intended to include monovalent heterocyclic aromatic ring moieties, being either monocyclic, bicyclic or polycyclic, e.g. selected from the group consisting of pyridinyl, 1-H-tetrazol-5-yl, thiazolyl, imidazolyl, indolyl, pyrimidinyl, thiadiazolyl, pyrazolyl, oxazolyl, isoxazolyl, oxadiazolyl, thienyl, quinolinyl, pyrazinyl, or isothiazolyl, optionally substituted with one or more $C_{1-6}$-alkyl, $C_{1-6}$-alkoxy, halogen, amino or aryl.

The term "halogen" is intended to include chlorine (Cl), fluorine (F), bromine (Br) and iodine (I).

The compounds of the present invention may optionally be on a pharmaceutically acceptable salt form such as the pharmaceutically acceptable acid addition salts of compounds of formula I which include those prepared by reacting the compound of formula I with an inorganic or organic acid such as hydrochloric, hydrobromic, sulfuric, acetic, phosphoric, lactic, malic, maleic, mandelic, phthalic, citric, glutaric, gluconic, methanesulfonic, salicylic, succinic, tartaric, toluenesulfonic, trifluoroacetic, sulfamic or fumaric acid and/or water.

The compounds of formula I may be administered in pharmaceutically acceptable acid addition salt form or, where appropriate, as an alkali metal or alkaline earth metal or lower alkylammonium salt. Such salt forms are believed to exhibit approximately the same order of activity as the free base forms.

In another aspect, the present invention relates to a pharmaceutical composition comprising, as an active ingredient, a compound of the general formula I or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences,* 1985 or in Remington: The Science and Practice of Pharmacy, 19th Edition (1995). The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 10 mg |
| Colloidal silicon dioxide (Aerosil) | 1.5 mg |
| Cellulose microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

It has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or in livestock. Furthermore, the compounds of the general formula I have a high oral efficacy.

Thus, in a particular aspect, the present invention relates to a pharmaceutical composition for stimulating the release of growth hormone from the pituitary, the composition comprising, as an active ingredient, a compound of the general formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary.

To those skilled in the art, it is well known that the current and potential uses of growth hormone in humans are varied and multitudinous. Thus, compounds of formula I can be administered for purposes stimulating release of growth hormone from the pituitary and would then have similar effects or uses as growth hormone itself. Compounds of formula I are useful for: stimulation of growth hormone release in the elderly, prevention of catabolic side effects of glucocorticoids, prevention and treatment of osteoporosis, treatment of chronic fatigue syndrom (CFS), treatment of acute fatigue syndrom and muscle loss following elective surgery, stimulation of the immune system, acceleration of wound healing, accelerating bone fracture repair, accelerating complicated fractures, e.g. distraction osteogenesis, treatment of wasting secondary to fractures, treatment of growth retardation, treating growth retardation resulting from renal failure or insufficiency, treatment of cardiomyopathy, treatment of wasting in connection with chronic liver disease, treatment of thrombocytopenia, treatment of growth retardation in connection with Crohn's disease, treatment of short bowel syndrome, treatment of wasting in connection with chronic obstructive pulmonary disease (COPD), treatment of complications associated with transplantation, treatment of physiological short stature including growth hormone deficient children and short stature associated with chronic illness, treatment of obesity and growth retardation associated with obesity, treatment of anorexia, treating growth retardation associated with the Prader-Willi syndrome and Turner's syndrome; increasing the growth rate of a patient having partial growth hormone insensitive syndrome, accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of catabolism in connection with pulmonary dysfunction and ventilator dependency; treatment of cardiac failure or related vascular dysfunction, treatment of impaired cardiac function, treatment or prevention of myocardial infarction, lowering blood pressure, protection against ventricular dysfunction or prevention of reperfusion events; treatment of adults in chronic dialysis; attenuation of protein catabolic responses after major surgery, reducing cachexia and protein loss due to chronic illness such as cancer or AIDS; treatment of hyperinsulinemia including nesidioblastosis, adjuvant treatment for ovulation induction; stimulation of thymic development and prevention of the age-related decline of thymic function, treatment of immunosuppressed patients; treatment of sarcopenia, treatment of wasting in connection with AIDS; improvement in muscle strength, mobility, maintenance of skin thickness, metabolic homeostasis and renal homeostasis in the frail elderly, stimulation of osteoblasts, bone remodelling and cartilage growth; regulation of food intake; stimulation of the immune system in companion animals and treatment of disorder of aging in companion animals, promoting growth in livestock and stimulation of wool growth in sheep, increasing milk production in livestock, treatment of metabolic syndrom (syndrome X), treatment of insulin resistance, including NIDDM, in mammals, e.g. humans, treatment of insulin resistance in the heart, improvement of sleep quality and correction of the relative hyposomatotropism of senescence due to high increase in REM sleep and a decrease in REM latency, treatment of hypothermia, treatment of frailty associated with aging, treatment of congestive heart failure, treatment of hip fractures, treatment of immune deficiency in individuals with a depressed T4/T8 cell ratio, treatment of muscular atrophy, treatment of musculoskeletal impairment in elderly, enhancing the activity of protein kinase B (PKB), improvement of the overall pulmonary function, treatment of sleep disorders, treatment of growth retardation in connection with asthma, treatment of growth retardation in connection with juvenile rheumatic arthritis, and treatment of growth retardation in connection with systic fibrosis.

For the above indications the dosage will vary depending on the compound of formula I employed, on the mode of administration and on the therapy desired. However, generally dosage levels between 0.0001 and 100 mg/kg body weight daily are administered to patients and animals to obtain effective release of endogenous growth hormone. Morever the compounds of formula I have no or substantially no side-effects, when administered in the above dosage levels, such side-effects being e.g. release of LH, FSH, TSH, ACTH, vasopressin, oxytocin, cortisol and/or prolactin. Usually, dosage forms suitable for oral, nasal, pulmonal or transdermal administration comprise from about 0.0001 mg to about 100 mg, preferably from about 0.001 mg to about 50 mg of the compounds of formula I admixed with a pharmaceutically acceptable carrier or diluent.

The dosage of the compounds according to this invention is suitably 0.01–500 mg/day, e.g. from about 5 to about 50 mg, such as about 10 mg per dose, when administered to patients, e.g. humans, as a drug.

Optionally, the pharmaceutical composition of the invention may comprise a compound of formula I combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the compounds of formula 1, they may be useful in vitro tools for investigating the regulation of growth hormone release.

Compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients pituitary to release growth hormone.

Compounds of formula I may be administered to commercially important animals to increase their rate and extent of growth, and to increase milk and wool production.

A further use of growth hormone secretagogue compounds of formula I is in combination with other secretagogues such as GHRP (2 or 6), GHRH and its analogues, growth hormone and its analogues or somatomedins including IGF-1 and IGF-2.

Pharmacological Methods

Compounds of formula I may be evaluated in vitro for their efficacy and potency to release growth hormone in rat pituitary primary cultures, and such evaluation may be performed as described below.

The isolation of rat pituitary cells is a modification of O. Sartor et al., *Endocrinology* 116, 1985, pp. 952–957. Male albino Sprague-Dawley rats (250+/−25 grams) were purchased from Mollegaard, Lille Skensved, Denmark. The rats were housed in group cages (four animals/cage) and placed in rooms with 12 hour light cycle. The room temperature varied from 19–240° C. and the humidity from 30–60%.

The rats were decapitated and the pituitaries dissected. The neurointermediate lobes were removed and the remaining tissue was immediately placed in icecold isolation buffer (Gey's medium (Gibco 041-04030) supplemented with 0.25% Dglucose, 2% non-essential amino acids (Gibco 043-01140) and 1% bovine serum albumine (BSA) (Sigma A-4503)). The tissue was cut into small pieces and transferred to isolation buffer supplemented with 3.8 mg/ml of trypsin (Worthington #3707 TRL-3) and 330 mg/ml of DNase (Sigma D-4527). This mixture was incubated at 70 rotations/min for 35 min at 37° C. in a 95/5% atmosphere of $O_2/CO_2$. The tissue was then washed three times in the above buffer. Using a standard pasteur pipette, the tissue was then aspirated into single cells. After dispersion, cells were filtered through a nylon filter (160 mm) to remove undigested tissue. The cell suspension was washed 3 times with isolation buffer supplemented with trypsin inhibitor (0.75 mg/ml, Worthington #2829) and finally resupended in culture medium; DMEM (Gibco 041-01965) supplemented with 25 mM HEPES Sigma H-3375), 4 mM glutamine (Gibco 043-05030H), 0.075% sodium bicarbonate (Sigma S-875), 0.1% non-essential amino acid, 2.5% fetal calf serum (FCS, Gibco 011-06290), 3% horse serum (Gibco 034-06050), 10% fresh rat serum, 1 nM $T_3$ (Sigma T-2752) and 40 mg/l dexamethasone (Sigma D-4902) pH 7.3, to a density of $2 \times 10^5$ cells/ml. The cells were seeded into microtiter plates (Nunc, Denmark), 200 ml/well, and cultured for 3 days at 37° C. and 8% $CO_2$.

Compound Testing

After culturing, the cells were washed twice with stimulation buffer (Hanks Balanced Salt Solution (Gibco 041-04020) supplemented with 1% BSA (Sigma A-4503), 0.25% D-glucose (Sigma G-5250) and 25 mM HEPES (Sigma H-3375) pH 7.3) and preincubated for 1 hour at 37° C. The buffer was exchanged with 90 ml stimulation buffer (37° C.). Ten ml test compound solution was added and the plates were incubated for 15 min at 37° C. and 5% $CO_2$. The medium was decanted and analyzed for GH content in an rGH SPA test system.

All compounds were tested in doses ranging from 10 pM to 100 mM. A dose-response relation was constructed using the Hill equation (FIG. P, Biosoft). The efficacy (maximal GH released, $E_{max}$) was expressed in % of the $E_{max}$ of GHRP-6. The potency ($EC_{50}$) was determined as the concentration inducing half maximal stimulation of the GH release.

Compounds of Formula I May be Evaluated for Their Metabolic Stability Using the Procedure Described Below Compounds is dissolved at a concentration of 1 mg/ml in water. 25 ml of this solution is added to 175 ml of the respective enzyme-solution (resulting in an enzyme:substrate ratio (w/w) of approximately 1:5). The solution is left at 37° C. overnight. 10 ml of the various degradation solutions is analyzed against a corresponding zero-sample using flow injection electrospray mass spectrometry (ESMS) with selected ion monitoring of the molecular ion. If the signal has decreased more than 20% compared to the zero-sample, the remainder of the solution is analyzed by HPLC and mass spectrometry in order to identify the extent and site(s) of degradation precisely.

Several standard peptides (ACTH 4–10, Angiotensin 1–14 and Glucagon) have been included in the stability tests in order to verify the ability of the various solutions to degrade peptides.

Standard peptides (angiotensin 1–14, ACTH 4–10 and glucagon) were purchased from Sigma, Mo., USA)

Enzymes (trypsin, chymotrypsin, elastase aminopeptidase M and carboxypeptidase Y and B) were all purchased from Boehringer Mannheim GmbH (Mannheim, Germany)

Pancreatic enzyme mix: trypsin, chymotrypsin and elastase in 100 mM ammoniumbicarbonate pH 8.0 (all concentrations 0.025 mg/ml).

Carboxypeptidase mix: carboxypeptidase Y and B in 50 mM ammoniumacetate pH 4.5 (all concentrations 0.025 mg/ml).

Aminopeptidase M solution: aminopeptidase M (0.025 mg/ml) in 100 mM ammoniumbicarbonate pH 8.0

Mass spectrometric analysis was performed using two different mass spectrometers. A Sciex API III triple quadrupole LC-MS instrument (Sciex instruments, Thornhill, Ontario) equipped with an electrospray ion-source and a Bio-Ion 20 time-of-flight Plasma Desorption instrument (Bio-Ion Nordic AB, Uppsala, Sweden).

Quantification of the compounds (before and after degradation) was done on the API III instrument using single ion monitoring of the molecular ion in question with flow injection of the analyte. The liquid flow (MeOH:water 1:1) of 100 ml/min was controlled by an ABI 140B HPLC unit (Perkin-Elmer Applied Biosystems Divisions, Foster City, Calif.). The instrument parameters were set to standard operation conditions, and SIM monitoring was performed using the most intense molecular ion (in most cases this corresponded to the doubly charged molecular ion).

Identification of degradation products furthermore involved the use of plasma desorption mass spectrometry (PDMS) with sample application on nitrocellulose coated targets and standard instrumental settings. The accuracy of the hereby determined masses is generally better than 0.1%.

Separation and isolation of degradation products was done using a HY-TACH C-18 reverse phase 4.6×105 mm HPLC column (Hewlett-Packard Company, Palo Alto, Calif.) with a standard acetonitril: TFA separation gradient. The HPLC system used was HP1090M (Hewlett-Packard Company, Palo Alto, Calif.).

| Peptide derivative | MW/SIM ion (amu) | Carboxy-peptidase mix | Pan. enzyme mix |
|---|---|---|---|
| Standards | | | |
| ACTH 4-10 | 1124.5/562.8 | + | − |
| Glucagon | 3483/871.8 | − | − |
| Insulin (B23-29) | 859.1/430.6 | | |
| Angiotensin 1-14 | 1760.1/881.0 | − | − |
| GHRP-2 | 817.4/409.6 | − | − |
| GHRP-6 | 872.6/437.4 | − | − |

+ Stable (less than 20% decrease in SIM signal after 24 h in degradation solution)
− Unstable (more than 20% decrease in SIM signal after 24 h in degradation solution)

Any novel feature or combination of features described herein is considered essential to this invention.

EXAMPLES

The process for preparing compounds of formula I and preparations containing them is further illustrated in the following examples, which however, are not to be construed as limiting.

The structures of the compounds are confirmed by either elemental analysis (MA) nuclear magnetic resonance (NMR) or mass spectrometry (MS). NMR shifts (δ) are given in parts per million (ppm) and only selected peaks are given. mp is melting point and is given in ° C. Column chromatography was carried out using the technique described by W. C. Still et al, J. Org. Chem. 1978, 43, 2923–2925 on silica gel 60. Compounds used as starting materials are either known compounds or compounds which can readily be prepared by methods known per se.

HPLC-Analysis
Method A1

The RP-analysis was performed using UV detections at 214, 254, 276, and 301 nm on a 218TP54 4.6 mm×250 mm 5 m C-18 silica column (The Seperations Group, Hesperia), which was eluted at 1 mL/min at 42° C. The column was equilibrated with 5% acetonitrile in a buffer consisting of 0.1 M ammonium sulfate, which was adjusted to pH 2.5 with 4M sulfuric acid. after injection the sample was eluted by a gradient of 5% to 60% acetonitrile in the same buffer during 50 min.

Method B1

The RP-analysis was performed using UV detections at 214, 254, 276, and 301 nm on a 218TP54 4.6 mm×250 mm 5 m C-18 silica column (The Seperations Group, Hesperia), which was eluted at 1 mL/min at 42° C. The column was equilibrated with 5% (acetonitrile+0.1% TFA) in an aqueous solution of TFA in water (0.1%). After injection the sample was eluted by a gradient of 5% to 60% (acetonitrile+0.1% TFA) in the same aqueous buffer during 50 min.

Abbreviations:
TLC: thin layer chromatography
DMSO: dimethylsulfoxide
min: minutes
h: hours
Boc: tert butyloxycarbonyl
DMF: dimethylformamide
THF: tetrahydrofuran
EDAC: N-ethyl-N'-dimethylaminopropylcarbodiimide hydrochloride
HOAt: 1-hydroxy-7-azabenzotriazole
DIEA: diisopropylethylamine
TFA: trifluoroacetic acid Buildingblocks:
N-methylated aminoacids used in the following examples were prepared as in Can. J. Chem. 1977, 55, 906.

3-Hydroxy-1,1-dimethylpropylcarbamic acid tert-butyl ester:

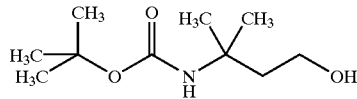

At 0° C., ethyl chloroformate (1.10 mL, 11.5 mmol) was given dropwise to a solution of 3-tert-butoxycarbonylamino-3-methylbutanoic acid (2.50 g, 11.5 mmol) and triethylamine (1.92 mL, 13.8 mmol) in tetrahydrofuran (10 mL). The solution was stirred for 40 min at 0° C. The formed precipitate was filtered off and washed with tetrahydrofuran (20 mL). The liquid was immediately cooled to 0° C. A 2M solution of lithium boronhydride in tetrahydrofuran (14.4 mL, 28.8 mmol) was added dropwise. The solution was stirred at 0° C. for 2 h, and then warmed to room temperature. over a period of 4 h. It was cooled to 0° C. Methanol (5 mL) was added carefully. 1N Hydrochloric acid (100 mL) was added. The solution was extracted with ethyl acetate (2×100 mL, 3×50 mL). The combined organic layers were washed with saturated sodium hydrogen carbonate solution (100 mL) and dried over magnesium sulfate. The solvent was removed in vacuo. The crude product was chromatographed on silica (110 g) with ethyl acetate/heptane 1:2 to give 1.84 g of 3-hydroxy-1,1-dimethylpropylcarbamic acid tert-butyl ester.

$^1$H-NMR (CDCl$_3$): δ1.33 (s, 6 H); 1.44 (s, 9 H); 1.88 (t, 2 H); 1.94 (br, 1 H); 3.75 (q, 2 H); 4.98 (br, 1 H).

3-(tert-Butoxycarbonylamino)-3-methylbutanal:

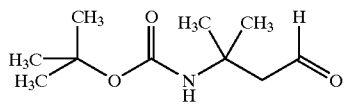

DMSO (1.22 mL, 17.2 mmol) was added to a solution of oxalyl chloride (1.1 mL, 12.9 mmol) at −78° C. in dichloromethane (15 mL). The mixture was stirred for 15 min at −78° C. A solution of 3-hydroxy-1,1-dimethylpropylcarbamic acid tert-butyl ester (1.75 g, 8.6 mmol) in dichloromethane (10 mL) was added dropwise over a period of 15 min. The solution was stirred at −78° C. for another 15 min. Triethylamine (6.0 mL, 43 mmol) was added. The solution was stirred at −78° C. for 5 min and then warmed to room temperature. The solution was diluted with dichloromethane (100 mL) and extracted with 1N hydrochloric acid (100 mL). The aqueous phase was extracted with dichloromethane (50 mL). The combined organic layers were washed with saturated sodium hydrogen carbonate solution (100 mL) and dried over magnesium sulfate. The solvent was removed in vacuo. The crude product was purified by column chromatography on silica (140 g) with ethyl acetate/heptane (1:3) to give 1.10 g of 3-(tert-butoxycarbonylamino)-3-methylbutanal.

MHz-$^1$H-NMR (CDCl$_3$): δ1.39 (s, 6 H); 1.45 (s, 9 H); 2.85 (d, 2 H); 4.73 (br. 1 H); 9.80 (t, 1 H).

Ethyl (2E)-5-(tert-Butoxycarbonylamino)-5-methylhex-2-enoate:

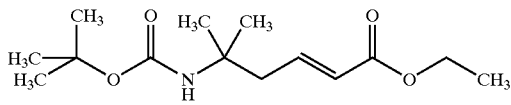

Triethylphoshonoacetate (1.96 ml, 9.8 mmol) was dissolved in tetrahydrofuran (30 ml). Potassium tert-butoxide (1.10 g, 9.8 mmol) was added. The solution was stirred for 40 min at room temperature. A solution of 3-(tert-butoxycarbonylamino)-3-methylbutanal (1.10 g, 5.5 mmol) in Tetrahydrofuran (6 ml) was added. The solution was stirred at room temperature. for 75 min. It was diluted with ethyl acetate (100 ml) and 1N hydrochloric acid (100 ml). The phases were separated. The aqueous phase was extracted with ethyl acetate (2×50 ml). The combined organic phases were washed with saturated sodium hydrogen carbonate solution (60 ml) and dried over magnesium sulfate. The solvent was removed in vacuo. The crude product was purified by column chromatography on silica (90 g) with ethyl acetate/hepatane (1:4) to give 1.27 g of ethyl (2E)-5-(tert-butoxycarbonylamino)-5-methylhex-2-enoate.

$^1$H-NMR (CDCl$_3$): δ1.30 (s, 6 H); 1.30 (t, 3 H); 1.46 (s, 9 H); 2.62 (d, 2 H); 4.27 (q, 2 H); 4.42 (br, 1 H); 5.88 (d, 1 H); 6.94 (td, 1 H).

(2E)-5-(tert-Butoxycarbonylamino)-5-methylhex-2-enoic acid:

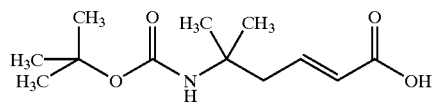

Ethyl (2E)-5-(tert-butoxycarbonylamino)-5-methylhex-2-enoate (1.233 g, 4.54 mmol) was dissolved in dioxane (20 ml). Lithium hydroxide (0.120 g, 5.00 mmol) was added as a solid. Water (10 ml) was added, until a clear solution was reached. The solution was stirred 16 h at room temperature. The solution was diluted with water (70 ml) and was extracted with tert-butyl methyl ether (2×100 ml). The aqueous phase was acidified with 1N sodium hydrogensulfate solution (pH=1) and was extracted with tert-butylmethylether (3×70 ml). The organic phases were combined and dried over magnesium sulfate. The solvent was removed in vacuo to give 1.05 g of (2E)-5-(tert-butoxycarbonylamino)-5-methylhex-2-enoic acid. The crude product was used for further syntheses.

$^1$H-NMR (DMSO d$_6$): δ1.15 (s, 6 H); 1.35 (s, 9 H); 2.53 (d, 2 H); 5.75 (d, 1 H); 6.57 (br, 1 H); 6.75 (td, 1 H); 12.15 (s, 1 H).

Example 1

(2E)-5-Amino-5-methylhex-2-enoic acid N-methyl-N-[(1R)-1-(N-methyl-N-{(1R)-1-[N-methyl-N-(2-(2-pyridinyl)ethyl)carbamoyl]-2-phenylethyl}carbamoyl)-2-(2-naphthyl)ethyl]amide.

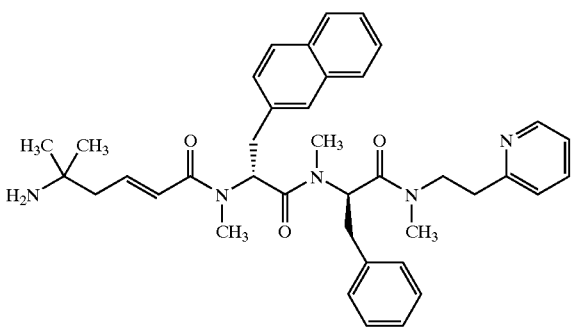

Step 1.
N-Methyl-N{(1R)-1-[N-methyl-N-(2-(2-pyridyl)ethyl)carbamoyl]-2-phenylethyl}carbamic acid tert-butyl ester.

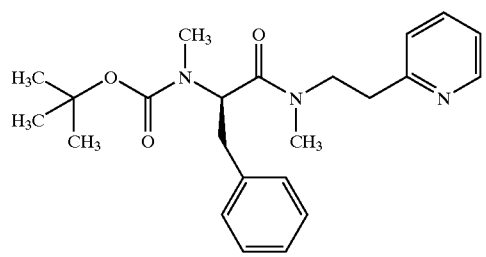

(2R)-2-(N-(tert-Butoxycarbonyl)-N-methylamino)-3-phenylpropionic acid (11.2 g, 40 mmol), 1-hydroxy-7-azabenzotriazole (5.4 g, 40 mmol) and N-(3-dimethylaminopropyl)-N'-ethylcarbodiimide hydrochloride (7.7 g, 40 mmol) were dissolved in dichloromethane (100 mL). The reaction mixture was stirred for 15 min. Ethyidiisopropylamine (6.85 mL, 40 mmol) and 2-(2-methylaminoethyl)pyridine (5.54 mL, 40 mmol) were added. The reaction mixture was stirred for 16 h. The reaction mixture was washed with sat. aqueous sodium hydrogen carbonate solution (3×150 mL). The organic layer was dried over magnesium sulfate. The solvent was removed in vacuo. The crude product was purified by flash chromatography on silica (400 g), using ethyl acetate as eluent, to give 10.9 g of N-methyl-N{(1R)-1-[N-methyl-N-(2-(2-pyridyl)ethyl)carbamoyl]-2-phenylethyl}carbamic acid tert-butyl ester.

¹H-NMR (CDCl₃): δ1.12, 1.20, 1.30 and 1.35 (all s, together 9 H); 2.75–3.20 (m, together 10 H); 3.50–4.00 (m, together 2 H), 4.95, 5.23 and 5.39 (m,t and t, together 1 H); 7.00–7.30 (m, together 7 H); 7.55 (m, 1 H); 8.51 (br m, 1 H)

Step 2.
(2R)-N-Methyl-2-(methylamino)-3-phenyl-N-(2-(2-pyridyl)ethyl)propionamide.

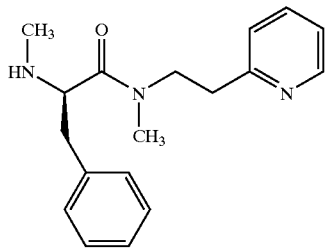

N-Methyl-N{(1R)-1-[N-methyl-N-(2-(2-pyridyl)ethyl) carbamoyl]-2-phenylethyl}carbamic acid tert-butyl ester was dissolved in dichloromethane (75 mL). Trifluoroacetic acid (75 mL, 0.978 mol) was added to the stirred solution. The reaction mixture was stirred for 40 min. The solvent was removed in vacuo. The product was dissolved in dichloromethane (30 mL) and sat. aqueous sodium hydrogen carbonate solution (20 mL). The reaction mixture was neutralised with solid sodium hydrogen carbonate. Dichloromethane (100 mL) was added and the aqueous phase was extracted with dichloromethane (2×150 mL). The combined organic layers were dried over magnesium sulfate. The solvent was removed in vacuo, to give 7.9 g of (2R)-N-Methyl-2-(methylamino)-3-phenyl-N-(2-(2-pyridyl)ethyl) propionamide.

¹H-NMR (CDCl₃): δ2.10 and 2.27 (both s, together 3 H); 2.51 and 2.87 (both s, together 3 H); 2.60–3.20 (m, together 4 H); 3.50–3.75 (m, together 3 H); 6.97–7.3 (m, together 7 H); (m, 1 H); 8.50 (dd, 1 H)

Step 3.
N-Methyl-N-[(1R)1-(N-methyl-N-{(1R)-1-[N-methyl-N-(2-(pyridinyl)ethyl)carbamoyl]-2-phenylethyl}carbamoyl)-2-(2-naphthyl)ethyl]carbamic acid tert-butyl ester.

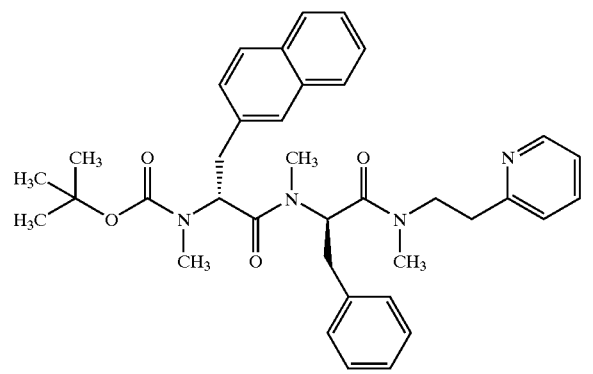

(2R)-2-(N-(tert-butoxycarbonyl)-N-methylamino)-3-(2-naphthyl) propionic acid (11.2 g, 34 mmol), 1-hydroxy-7-azabenzotriazole (5.2 g, 38 mmol) and N-(3-dimethylaminopropyl)-N'-ethylcarbodiimide hydrochloride (6.9 g, 36 mmol) were dissolved in dichloromethane (100 mL). The reaction mixture was stirred for 15 min. Ethyldiisopropylamine (7.0 mL, 41 mmol) was added. (2R)-N-Methyl-2-(methylamino)-3-phenyl-N-(2-(2-pyridyl)ethyl) propionamide (7.9 g, 27 mmol) dissolved in dichloromethane (20 mL) was added. The reaction mixture was stirred for 16 h. The reaction mixture was added to aminomethylresin (17.3 g, 13.5 mmol). The reaction mixture was stirred for 6 h. The reaction mixture was filtrated. The organic layer was washed with sat. aqueous sodium hydrogen carbonate solution (2×150 mL). The organic layer was dried over magnesium sulfate. The solvent was removed in vacuo. The crude product was purified by flash chromatography on silica (400 g), using ethyl acetate as eluent, to give 14.9 g N-Methyl-N-[(1R)1-(N-methyl-N-{(1R)-1-[N-methyl-N-(2-(pyridinyl)ethyl)carbamoyl]-2-phenylethyl}carbamoyl)-2-(2-naphthyl)ethyl]carbamic acid tertbutyl ester.

¹H-NMR (CDCl₃): δ1.07, 1.15, 1.33 and 1.40 (all s, together 9 H); 1.80–3.75 (m, together 17 H); 5.00, 5.35, 5.59, 5.70 and 5.85 (m, together 2 H); 6.85–7.80 (m, together 15 H); 8.40–8.57 (m, together 1 H).

Step 4.
(2R)-N-Methyl-2-(methylamino)-N{(1R)-1-[N-methyl-N-(2-(pyridin-2-yl)ethyl)carbamoyl]-2-phenylethyl}3-(2-naphthyl)propionamide.

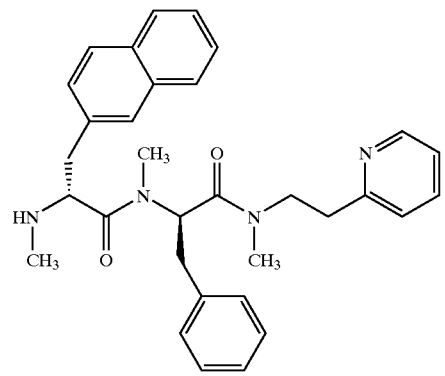

N-Methyl-N-[(1R)1-(N-methyl-N-{(1R)-1-[N-methyl-N-(2-(pyridinyl)ethyl)carbamoyl]-2-phenylethyl}carbamoyl)-2-(2-naphthyl)ethyl]carbamic acid tert-butyl ester (14.9 g, 24.5 mmol) was dissolved in dichloromethane (75 mL). Trifluoroacetic acid (75 mL, 0.978 mol) was added to the stirred solution. The reaction mixture was stirred for 40 min. The solvent was removed in vacuo. The product was dissolved in dichloromethane (50 mL) and sat. aqueous sodium hydrogen carbonate solution (40 mL). The mixture was neutralised with solid sodium hydrogen carbonate. Dichloromethane (100 mL) was added and the aqueous phase was extracted with dichloromethane (2×150 mL). The combined organic layers were dried over magnesium sulfate. The solvent was removed in vacuo, to give 11.9 g of (2R)-N-Methyl-2-(methylamino)-N-{(1R)-1-[N-methyl-N-(2-(pyridin-2-yl)ethyl)carbamoyl]-2-phenylethyl}-3-(2-naphthyl)propionamide.

¹H-NMR (CDCl₃): δ1.77, 1.87 and 1.97 (all s, together 4 H); 2.60 (s, 3 H); 2.70–3.20 (m, together 9 H); 3.52, 3.70 and 4.10 (t, m and m, together 2 H); 5.72–5.89 (m, 1 H); (m, together 15 H); 8.50 (dd, 1 H).

Step 5.
((3E)-1,1-Dimethyl-4-{N-methyl-N-[(1R)1-(N-methyl-N-{(1R)-1-[N-methyl-N-(2-(pyridin-2-yl)ethyl)carbamoyl]-2-phenylethyl}carbamoyl)-2-(2-naphthyl)ethyl]carbamoyl}but-3-enyl)carbamic acid tert-butyl ester.

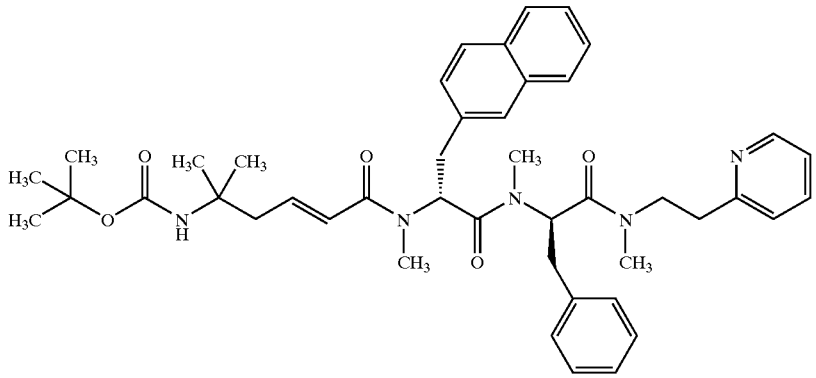

(2E)-5-(tert-Butoxycarbonylamino)-5-methylhex-2-enoic acid (2.87 g, 11.8 mmol), 1-hydroxy-7-azabenzotriazole (1.6 g, 11.8 mmol) and N-(3-dimethylaminopropyl)-N'-ethylcarbodiimide hydrochloride (2.26 g, 11.8 mmol) were dissolved in dichloromethane (30 mL). The reaction mixture was stirred for 15 min. Ethyidiisopropylamine (2.0 mL, 11.8 mmol) was added. (2R)-N-Methyl-2-(methylamino)-N-{(1R)-1-[N-methyl-N-(2-(pyridin-2-yl)ethyl)carbamoyl]-2-phenylethyl}-3-(2-naphthyl)propionamide (6.0 g, 11.8 mmol) dissolved in dichloromethan (10 mL) was added. The reaction mixture was stirred for 16 h. The reaction mixture was washed with sat. aqueous sodium hydrogen carbonate solution (100 mL). The aqueous phase was extracted with dichloromethane (100 mL). The combined organic layers were dried over magnesium sulfate. The solvent was removed in vacuo. The crude product was purified by flash chromatography on silica (400 g), using ethyl acetate as eluent, to give 5.28 g of ((3E)-1,1-Dimethyl-4-{N-methyl-N-[(1R)1-(N-methyl-N{(1R)-1-[N-methyl-N-(2-(pyridin-2-yl)ethyl)carbamoyl]-2-phenylethyl}carbamoyl)-2-(2-naphthyl)ethyl]carbamoyl}but-3-enyl)carbamic acid tert-butyl ester.

$^1$H-NMR (CDCl$_3$): δ1.17–1.29 (m, 6 H); 1.40 (s, 9 H); 2.40–3.10 (m, together 16 H); 3.37–3.75 (m, together 3 H); 4.40 (br m, 1 H); 5.55–5.37 (m, together 2 H); 6.03–6.19 (m, 1 H); 6.70–7.80 (m, together 15 H); 8.36–8.55 (m, together 1 H).

Step 6.
((3E)-1,1-Dimethyl-4-{N-methyl-N-[(1R)1-(N-methyl-N-{(1R)-1-[N-methyl-N-(2-(pyridin-2-yl)ethyl)carbamoyl]-2-phenylethyl}carbamoyl)-2-(2-naphthyl)ethyl]carbamoyl}but-3-enyl)carbamic acid tert-butyl ester (5.28 g, 7.2 mmol) was dissolved in dichloromethane (50 mL). The solution was cooled to −10° C. Trifluoroacetic acid (50 mL) was added to the stirred solution. The reaction mixture was stirred for 45 min at −10° C. The reaction mixture was added to a solution of ice, sodium hydrogen carbonate and water. The reaction mixture was neutralised with sodium hydrogen carbonate. Dichloromethane (400 mL) was added. The aqueous phase was extracted with dichloromethane (300 mL). The combined organic layers were dried over magnesium sulfate. The solvent was removed in vacuo. The crude product was purified by flash chromatography on silica (40 g), using 15% of a solution, 7% ammonium in ethanole, in dichloromethane as eluent, to give 3.2 g of the title compound.

$^1$H-NMR (CDCl$_3$): δ0.80–1.20 (m, together 6 H); 2.05–3.10 (m, together 17 H); 3.25–3.70 (m, together 3 H); 5.62, 5.70 and 5.85 (m,m and m, together 2 H); 6.03–6.17 (m, 1 H); 6.80–7.78 (m, together 15 H); 8.38–8.58 (m, 1 H)
MS: 634.2
HPLC: 28.243 min (A1)
28.963 min (B1)

For biological testing, the title compound was transferred into its acetate salt by lyophilization from 0.5 M acetic acid (100 mL)

Example 2

(2E)-5-Amino-5-methylhex-2-enoic acid N-methyl-N-[(1R)-1-(N-methyl-N-{(1R)1-[N-methyl-(2-(4-pyridinyl)ethyl)carbamoyl]-2-phenylethyl}carbamoyl)-2-(2-naphthyl)ethyl]amide

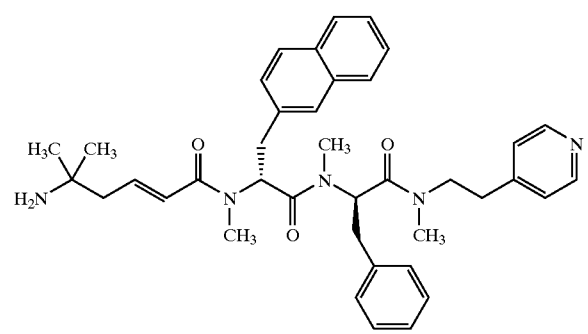

The title compound was prepared as in example 1 (except from step 3, see below) using 4-[2-(Methylamino)ethyl]pyridin, (2R)-2-(N-(tert-Butoxycarbonyl)-N-methylamino)-3-phenylpropionic acid, (2R)-2-(N-(tert-butoxycarbonyl)-N-methylamino)-3-(2-naphthyl)propionic acid and (2E)-5-(tert-Butoxycarbonylamino)-5-methylhex-2-enoic acid.

$^1$H-NMR (CDCl$_3$): δ1.15 (m, together 6 H); 1.95–3.70 (m, together 20 H); 5.59, 5.88 and 6.15 (all m, together 3 H); 6.78–8.56 (m, together 16 H)
MS: 634.4
HPLC: 27.597 min. (A1)
28.949 min. (B1)

Step 3.
N-Methyl-N-[(1R)-1-(N-methyl-N{(1R)-1-[N-methyl-N-(2-(pyridin-4-yl)ethyl)carbamoyl]-2-phenylethyl}carbamoyl)-2-(2-naphthyl)ethyl]carbamic acid tert-butyl ester.

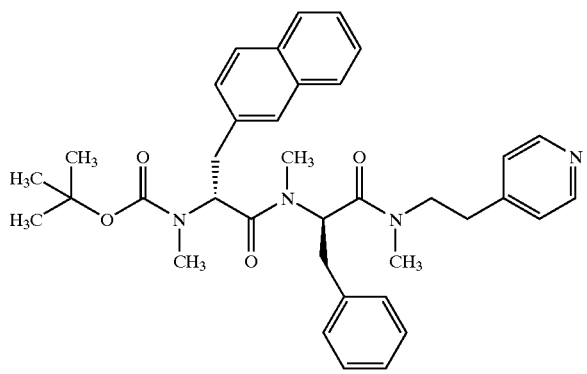

(2R)-2-(N-(tert-butoxycarbonyl)-N-methylamino)-3-(2-naphthyl)propionic acid (1.33 g, 4 mmol), 1-hydroxy-7-azabenzotriazole (549 mg, 4 mmol) and N-(3-dimethylaminopropyl)-N'-ethylcarbodiimide hydrochloride (775 mg, 4 mmol) were dissolved in dichloromethane (10 mL). The reaction mixture was stirred for 15 min. Ethyidiisopropylamine (0.692 mL, 4 mmol) was added. (2R)-N-methyl-2-(methylamino)-3-phenyl-N-(2-(pyridin-4-yl)-ethyl)propion amide (1.2 g, 4 mmol) dissolved in dichloromethane (15 mL) was added. The reaction mixture was stirred for 16 h. Dichloromethane (100 mL) was added. The organic layer was washed with sat. aqueous sodium hydrogen carbonate solution (50 mL). The aqueous phase was extracted with dichloromethane (2×50 mL). The combined organic layers were dried over magnesium sulfate. The solvent was removed in vacuo. The crude product was purified by flash chromatography on silica (40 g), using ethyl acetate as eluent, to give 1.16 g of N-Methyl-N-[(1R)-1-(N-methyl-N-{(1R)-1-[N-methyl-N-(2-(pyridin-4-yl)ethyl)carbamoyl]-2-phenylethyl}carbamoyl)-2-(2-naphthyl)ethyl]carbamic acid tert-butyl ester.

Comparison Example

The compound of example 1 was compared with the compound of example 408 disclosed in WO 9723508. The results are presented below:

| Compound | Structure | Oral bioavailability Fpo [%] | Plasma half-life T½ [h] |
|---|---|---|---|
| Example 1 | 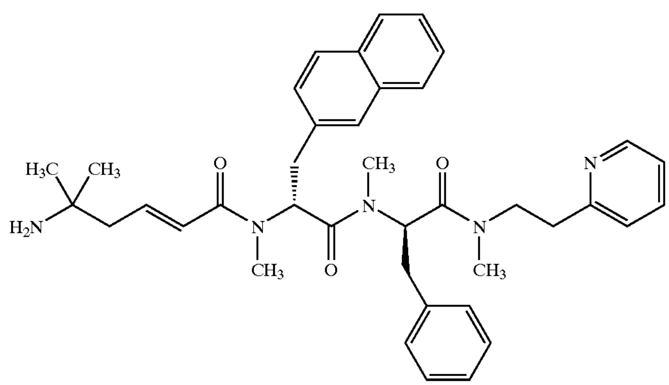 | 34 | 2.0 |
| Example 408 from WO 9723508 | 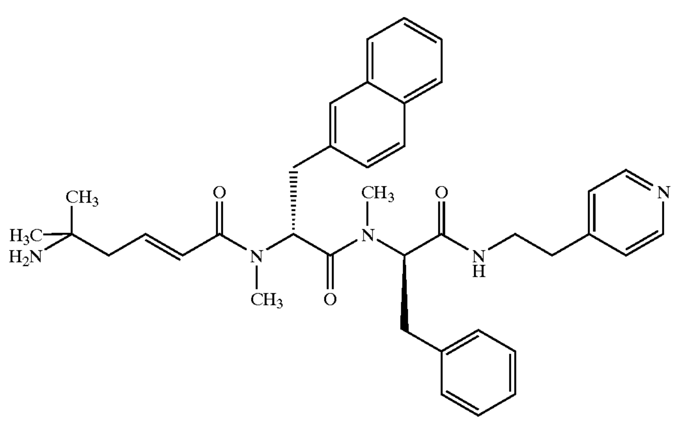 | 26 | 3.89 |

As can be seen, the compound of example 1 shows a better oral bioavailability and a shorter plasma half-life compared with the compound of example 408 from WO 9723508.

The pharmakokinetic data were obtained by following procedure:

The pharmacokinetics of the test compounds were investigated in fasted Beagle dogs.

Intravenous and oral administration of the test compound, in 5% glucose solution, was separated by a one weeks washout.

Blood samples were collected immediately before drug administration (time zero) and than 0.08, 0.25, 0.50, 0.75, 1.0, 1.5, 2.0, 3.0, 4.0, 5.0, and 6.0 hours after administration.

The plasma samples were stored frozen (<−18° C.) pending analysis.

An HPLC method with solid phase extraction and UV detection was used for the quantification of the compound in plasma.

The pharmacokinetic parameters for compounds were calculated by non-compartmental methods using the PC based pharmacokinetic software WinNonlin, version 1.1 (Scientific Consulting Inc., Apex, N.C., USA).

What is claimed is:

1. A compound of formula I

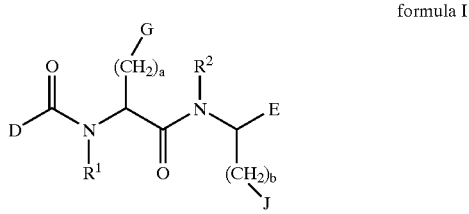

formula I wherein $R^1$ and $R^2$ are independently hydrogen or $C_{1-6}$-alkyl optionally substituted with aryl;

a and b are independently 1 or 2;

G is

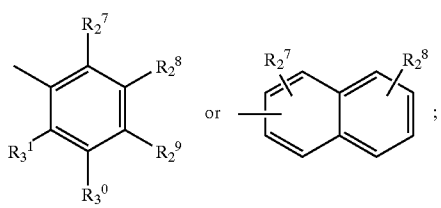

J is

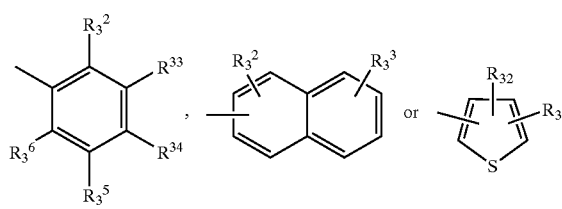

wherein $R^{27}$, $R^{28}$, $R^{29}$, $R^{30}$, $R^{31}$, $R^{32}$, $R^{33}$, $R^{34}$, $R^{35}$, and $R^{36}$ independently are hydrogen, halogen, aryl, $C_{1-6}$-alkyl or $C_{1-6}$-alkoxy;

D is $R^7$—NH—$(CR^8R^9)_p$—$(CH_2)_m$—M—$(CHR^{10})_q$—$(CH_2)_n$— wherein $R^7$, $R^8$, $R^9$ and $R^{10}$ are independently hydrogen or $C_{1-6}$ alkyl optionally substituted with halogen, amino, hydroxyl or aryl;

$R^7$ and $R^8$ or $R^7$ and $R^9$ or $R^8$ and $R^9$ may optionally form —$(CH_2)_i$—U—$(CH_2)_j$—, wherein i and j are independently are 1 or 2 and U is —O—, —S— or a valence bond;

m and n are independently 0, 1, 2, or 3;

p and q are independently 0 or 1;

M is —$CR^{11}$=$CR^{11a}$—, arylene, —O—, or —S—;

$R^{11}$ and $R^{11a}$ are independently hydrogen, or $C_{1-6}$-alkyl optionally substituted with aryl;

E is

—$CONR^{12}R^{13}$, wherein $R^{12}$ is $C_{1-6}$-alkyl;

$R^{13}$ is hetaryl or $C_{1-6}$-alkyl substituted with hetaryl;

or a pharmaceutically acceptable salt thereof.

2. The compound according to claim 1 wherein $R^1$ is methyl.

3. The compound according to claim 1 wherein $R^2$ is methyl.

4. The compound according to claim 1 wherein a is 1.

5. The compound according to claim 1 wherein b is 1.

6. The compound according to claim 1 wherein G is naphthyl.

7. The compound according to claim 1 wherein J is phenyl.

8. The compound according to claim 1 wherein M is —$CR^{11}$=$CR^{11a}$—.

9. The compound according to claim 1 wherein D is $H_2N$—$C(CH_3)_2$—$CH_2$—CH=CH—.

10. The compoupd according to claim 1 wherein E is —$CON(CH_3)R^{13}$ wherein $R^{13}$ is ethyl substituted with pyridinyl.

11. The compound according to claim 1 wherein

D is $H_2N$—$C(CH_3)_2$—$CH_2$—CH=CH—; and

E is —$CON(CH_3)R^{13}$ wherein $R^{13}$ is $C_{1-6}$-alkyl substituted with pyridinyl.

12. A compound according to claim 1 selected from the group consisting of (2E)-5-Amino-5-methylhex-2-enoic acid N-methyl-N-[(1R)-1-[N-methyl-N{( R)-1-(N-methyl-N-(2-(2-pyridinyl)ethyl)carbamoyl]-2-phenylethyl}carbamoyl)-2-(2-naphthyl)ethyl]amide

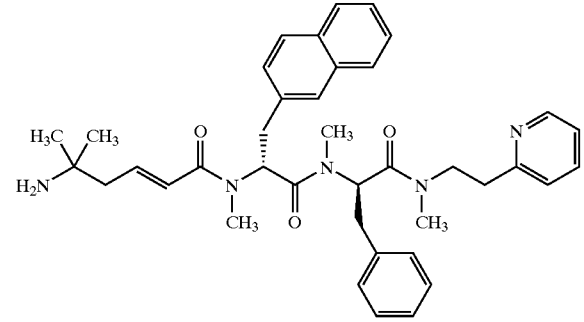

(2E)-5-Amino-5-methylhex-2-enoic acid N-methyl-N-[(1R)-1-(N-methyl-N-{(1R)-1-[N-methyl-N-(2-(4-pyridinyl)ethyl)carbamoyl]-2-phenylethyl}carbamoyl)-2-(2-naphthyl)ethyl]amide

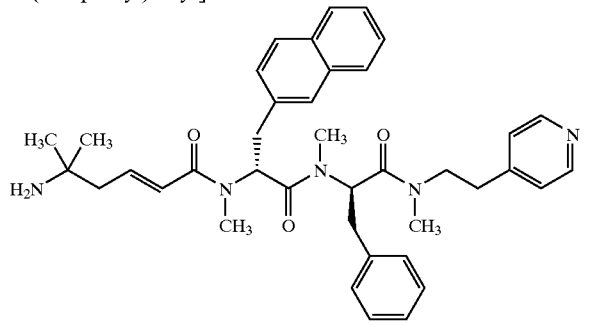

or a pharmaceutically acceptable salt thereof.

13. A composition comprising, as an active ingredient, a compound according to claim 1 or a pharmaceutically acceptable salt thereof together with a pharmaceutically acceptable carrier or diluent.

14. A method of stimulating the release of growth hormone from the pituitary of a mammal, comprising administering to a mammal in need thereof the compound according to claim 1 for a time and under conditions effective to stimulate release of growth homone from the pituitary of said mammal.

* * * * *